(12) United States Patent
Cobb et al.

(10) Patent No.: US 8,821,578 B2
(45) Date of Patent: Sep. 2, 2014

(54) INTERVERTEBRAL IMPLANT DEVICE FOR A POSTERIOR INTERBODY FUSION SURGICAL PROCEDURE

(75) Inventors: John Cobb, Lafayette, LA (US); William Atkinson, Lafayette, LA (US); Peter Harris, Boca Raton, FL (US)

(73) Assignee: U.S. Spine, Inc., Salt Lake City, UT (US)

( * ) Notice: Subject to any disclaimer, the term of this patent is extended or adjusted under 35 U.S.C. 154(b) by 136 days.

(21) Appl. No.: 12/896,292

(22) Filed: Oct. 1, 2010

(65) Prior Publication Data

US 2011/0245923 A1   Oct. 6, 2011

Related U.S. Application Data

(60) Provisional application No. 61/248,052, filed on Oct. 2, 2009.

(51) Int. Cl.
*A61F 2/44*   (2006.01)
*A61F 2/46*   (2006.01)
*A61F 2/30*   (2006.01)

(52) U.S. Cl.
CPC ............... *A61F 2/4465* (2013.01); *A61F 2/442* (2013.01); *A61F 2002/4629* (2013.01); *A61F 2002/30785* (2013.01); *A61F 2002/4475* (2013.01); *A61F 2002/30904* (2013.01); *A61F 2002/30878* (2013.01); *A61F 2002/30892* (2013.01); *A61F 2002/30779* (2013.01); *A61F 2/4611* (2013.01)
USPC .......................................... 623/17.16

(58) Field of Classification Search
CPC ....... A61F 2/44; A61F 2/4455; A61F 2/4465; A61F 2/447
USPC .............................. 623/17.11–17.16
See application file for complete search history.

(56) References Cited

U.S. PATENT DOCUMENTS 6,974,480 B2   12/2005   Messerli et al.
2007/0213826 A1*  9/2007   Smith et al. ................ 623/17.11

* cited by examiner

*Primary Examiner* — Matthew Lawson
(74) *Attorney, Agent, or Firm* — Phillips Ryther & Winchester; Matthew D. Thayne

(57) ABSTRACT

An intervertebral implant device is presented that may comprise a pair of substantially parallel opposed arcuate surfaces, a pair of substantially parallel opposed frictional surfaces each including a plurality of raised structures, a substantially curved end wall joining the par of parallel opposed arcuate surfaces, and a substantially recessed end wall joining the pair of parallel opposed arcuate surfaces. In certain embodiments, the intervertebral implant device defines one or more voids in which a bone graft material is selectively disposed. Preferably, the substantially recessed end wall is configured to selectively and pivotable receive one or more surgical implantation devices.

24 Claims, 19 Drawing Sheets

INTERVERTEBRAL IMPLANT DEVICE FOR A POSTERIOR INTERBODY FUSION SURGICAL PROCEDURE

CROSS-REFERENCE TO RELATED APPLICATION

The present patent application/patent claims the benefit of priority of U.S. Provisional Patent Application No. 61/248,052, filed on Oct. 2, 2009, and entitled "INTERVERTEBRAL IMPLANT DEVICE FOR A POSTERIOR INTERBODY FUSION SURGICAL PROCEDURE," the contents of which are incorporated in full by reference herein.

FIELD OF THE INVENTION

The present invention relates generally to an intervertebral implant device for a posterior interbody fusion surgical procedure. Advantageously, this intervertebral implant device is designed and configured such that it may be surgically implanted in the spine of a patient through a minimal access window, thereby sparing and preserving the associated facets to the greatest degree possible.

BACKGROUND OF THE INVENTION

A variety of spinal conditions, such as compression of the spinal cord nerve roots, degenerative disc disease, herniated nucleus pulposus, spinal stenosis, and spondylolisthesis may cause moderate to severe lower back and leg pain. Intervertebral or interbody fusion is a surgical procedure that is used to alleviate such lower back and leg pain. In posterior lumbar interbody fusion (PLIF), two adjacent vertebral bodies of the lumbar spine are fused together by removing the affected disc and inserting posteriorly one or more implant devices or cages that allow one or more bone grafts to grow between the two adjacent vertebral bodies to bridge the gap left by the removed disc. Various degrees of distraction may also be provided, as required on a case-by-case basis.

One variation of the traditional PLIF technique is the transforaminal posterior lumbar interbody fusion (T-PLIF) technique. In this surgical procedure, an implant device or cage is inserted into the affected disc space via a unilateral (or sometimes bilateral) posterior approach, offset from the midline of the spine, by first removing portions of the facets of the vertebrae. Advantageously, the T-PLIF technique avoids damage to nerve structures, such as the dura, cauda equina, and nerve roots, but the resulting transforaminal window available to remove the affected disc, prepare the vertebral endplates, and insert the implant device or cage is limited laterally by soft tissue and medially by the cauda equina.

A variety of different implant devices and cages typically used for the traditional PLIF procedure have also been used for the T-PLIF procedure with varying degrees of success. These include threaded titanium, ceramic, and polymer cages, allograft (i.e. bone) wedges, rings, etc. However, as these devices and cages are not designed specifically for the T-PLIF procedure, they are not shaped to be easily insertable into the affected disc space through the narrow transforaminal window, and may require additional refraction of the cauda equina and nerve roots. Such retraction may cause temporary or permanent nerve damage. In addition, some of these devices and cages, such as the threaded titanium, ceramic, and polymer cages, suffer from the disadvantage of requiring drilling and tapping of the vertebral endplates prior to insertion. Further, the incidence of subsidence in long term use is not known for such devices and cages. Finally, the restoration of lordosis, i.e. the natural curvature of the lumbar spine, is very difficult to achieve when a cylindrical or square titanium, ceramic, or polymer cage is used.

Thus, there is a need in the art for an intervertebral implant device for a posterior interbody fusion surgical procedure that is configured such that it may be surgically implanted in the spine of a patient through a minimal access window, thereby sparing and preserving the associated facets to the greatest degree possible.

BRIEF SUMMARY OF THE INVENTION

In various exemplary embodiments, the present invention provides an intervertebral implant device for a posterior interbody fusion surgical procedure. Advantageously, this intervertebral implant device is configured such that it may be surgically implanted in the spine of a patient through a minimal access window, thereby sparing and preserving the associated facets to the greatest degree possible.

In one exemplary embodiment, the present invention provides an intervertebral implant device, including: a pair of substantially parallel opposed arcuate surfaces; a pair of substantially parallel opposed frictional surfaces each including a plurality of raised structures; a substantially curved end wall joining the pair of parallel opposed arcuate surfaces; and a substantially recessed end wall joining the pair of parallel opposed arcuate surfaces; wherein the intervertebral implant device defines one or more voids in which a bone graft material is selectively disposed. The substantially recessed end wall is configured to selectively and pivotably receive one or more surgical implantation devices. The substantially curved end wall includes one or more smoothed edges. The substantially recessed end wall includes a first wall portion and a second wall portion arranged at an angle to one another and collectively forming a fish-tailed structure. The substantially recessed end wall includes one or more of a hole and a recess configured to selectively receive a surgical tool. The one or more voids defined by the intervertebral implant device pass through one or more of the pair of substantially parallel opposed arcuate surfaces and the pair of substantially parallel opposed frictional surfaces. The intervertebral implant device is configured to be selectively disposed in an intervertebral space through an access window formed through bony and soft tissue structures to either the left or right of a centerline of a spine.

In another exemplary embodiment, the present invention provides a surgical method for implanting an intervertebral implant device, including: providing an intervertebral implant device, including: a pair of substantially parallel opposed arcuate surfaces; a pair of substantially parallel opposed frictional surfaces each including a plurality of raised structures; a substantially curved end wall joining the pair of parallel opposed arcuate surfaces; and a substantially recessed end wall joining the pair of parallel opposed arcuate surfaces; wherein the intervertebral implant device defines one or more voids in which a bone graft material is selectively disposed; and disposing the intervertebral implant device within an intervertebral space through an access window formed adjacent to a facet joint of a spine of a patient. The substantially recessed end wall is configured to selectively and pivotably receive one or more surgical implantation devices. The substantially curved end wall includes one or more smoothed edges. The substantially recessed end wall includes a first wall portion and a second wall portion arranged at an angle to one another and collectively forming a fish-tailed structure. The substantially recessed end wall includes one or more of a hole and a recess configured to selectively receive a surgical tool. The one or more voids defined by the intervertebral implant device pass through one or more of the pair of substantially parallel opposed arcuate surfaces and the pair of substantially parallel opposed frictional surfaces. The intervertebral implant device is configured to be selectively disposed in an intervertebral space through the access window formed through bony and soft tissue structures to either the left or right of a centerline of a spine.

In a further exemplary embodiment, the present invention provides a surgical method for implanting an intervertebral implant device, including: forming an access window through bony and soft tissue structures to either the left or right of a centerline of a spine; passing bone graft material through the access window and into an adjacent intervertebral space; disposing bone graft material in an intervertebral implant device; passing the intervertebral implant device through the access window and into the adjacent intervertebral space; and positioning the intervertebral implant device within the intervertebral space. The intervertebral implant device includes: a pair of substantially parallel opposed arcuate surfaces; a pair of substantially parallel opposed frictional surfaces each including a plurality of raised structures; a substantially curved end wall joining the pair of parallel opposed arcuate surfaces; and a substantially recessed end wall joining the pair of parallel opposed arcuate surfaces. The intervertebral implant device defines one or more voids in which the bone graft material is selectively disposed.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

In various exemplary embodiments, the present invention provides an intervertebral implant device for a posterior interbody fusion surgical procedure. Advantageously, this intervertebral implant device is configured such that it may be surgically implanted in the spine of a patient through a minimal access window, thereby sparing and preserving the associated facets to the greatest degree possible.

Figure 1:
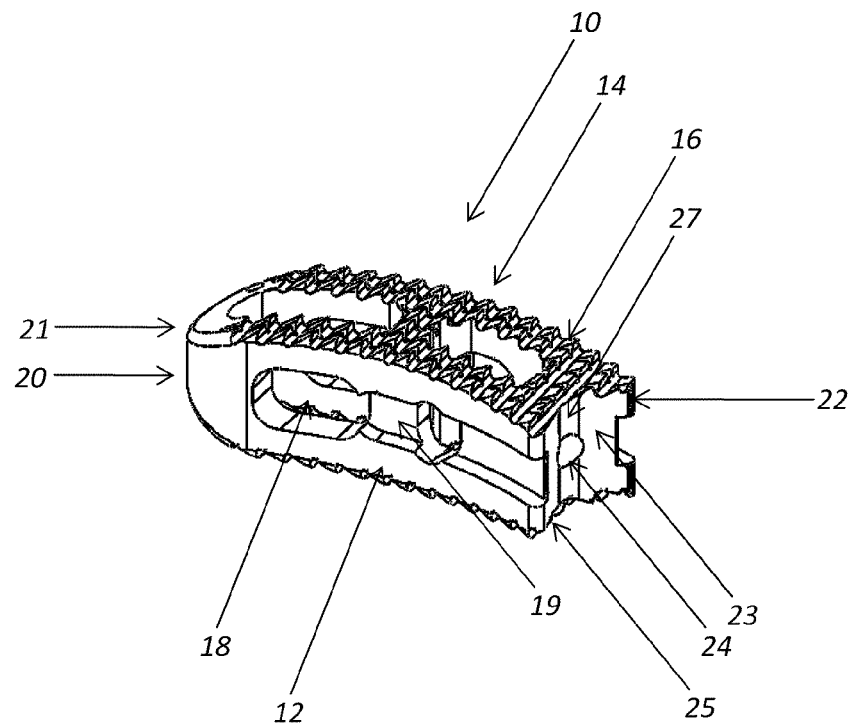
FIG. 1 is a perspective diagram illustrating one exemplary embodiment of the intervertebral implant device of the present invention.

FIG. 1 is a perspective diagram illustrating one exemplary embodiment of the intervertebral implant device 10 of the present invention. In this exemplary embodiment, the intervertebral implant device 10 includes a pair of substantially parallel opposed arcuate surfaces 12 and a pair of substantially parallel opposed frictional surfaces 14 including a plurality of raised structures 16, such as teeth, grooves or the like. The pair of opposed arcuate surfaces 12 and the pair of opposed frictional surfaces 14 together form a prismatic structure that has a slight curve in one plane. This prismatic structure has overall dimensions on the order of tens of mm in length, tens of mm in width, and several mm in thickness, such that it may be disposed in a range of intervertebral spaces and provide a range of distraction, if so desired. Preferably, the prismatic structure defines one or more voids 18 in which a bone graft material or the like may selectively be disposed. These voids 18 may be internal to the prismatic structure, pass through the pair of opposed arcuate surfaces 12, pass through the pair of opposed frictional surfaces 14, and/or be in communication with one or more recesses 19 manufactured into the exterior of the pair of opposed arcuate surfaces 12 and/or the pair of opposed frictional surfaces 14. These voids 18 and/or recesses 19 help promote bony ingrowth that eventually fuses the intervertebral implant device 10 in the intervertebral space. One end of the intervertebral implant device 10 includes a rounded or partially-rounded end wall 20, that preferably has smoothed edges 21 to prevent it from catching on or damaging any anatomical structures during insertion. The other end of the intervertebral implant device 10 includes a recessed or fish-tailed end wall 22. The fish-tailed end wall 22 defines a hole and/or other retention structures 24 for selectively and pivotably receiving one or more surgical implantation devices. In this exemplary embodiment, the fish-tailed end wall 22 includes a pair of angularly disposed walls 23,25 joined by a central flat wall 27. The first of the pair of angularly disposed walls 23 protrudes from the prismatic structure to a greater degree than the second of the pair of angularly disposed walls 25, although other suitable configurations may be utilized. In this exemplary embodiment, the retention structures 24 for selectively and pivotably receiving one or more surgical implantation devices are coextensive with the one or more recesses 19 manufactured into the exterior of the pair of opposed arcuate surfaces 12 and/or the pair of opposed frictional surfaces 14. The intervertebral implant device 10 may be made of any suitable surgically-implantable material, such as a metallic material, a ceramic material, a polymeric material, or an allograft material, and may have any suitable dimensions such that it may be disposed within an intervertebral space of the spine of a patient while providing a desired degree of distraction.

Advantageously, the configuration of the pair of substantially parallel opposed arcuate surfaces 12 and the pair of substantially parallel opposed frictional surfaces 14 provides a surgical implant that may be placed into the intervertebral space through a narrow transforaminal window or the like that is disposed either to the left or the right of the spinal centerline. This is due to the fact that the prismatic structure is symmetric top-to-bottom. Once placed, the plurality of raised structures 16 of the pair of substantially parallel opposed frictional surfaces 14 engage the intervertebral endplates, securing the intervertebral implant device 10 snugly in place.

Figure 2:
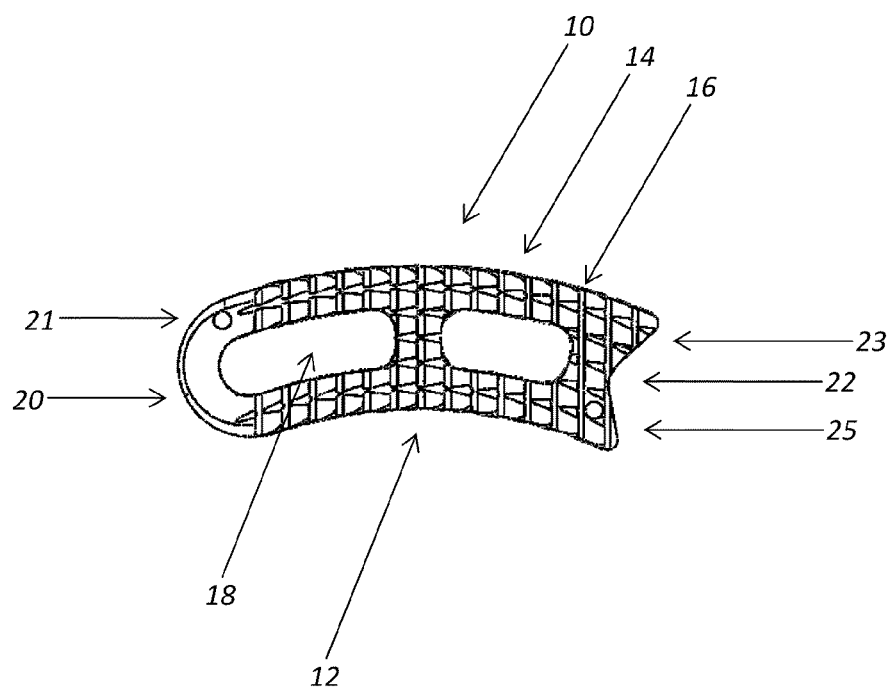
FIG. 2 is a planar diagram also illustrating one exemplary embodiment of the intervertebral implant device of the present invention.

FIG. 2 is a planar diagram also illustrating one exemplary embodiment of the intervertebral implant device 10 of the present invention. Again, in this exemplary embodiment, the intervertebral implant device 10 includes a pair of substantially parallel opposed arcuate surfaces 12 and a pair of substantially parallel opposed frictional surfaces 14 including a plurality of raised structures 16, such as teeth, grooves or the like. The pair of opposed arcuate surfaces 12 and the pair of opposed frictional surfaces 14 together form a prismatic structure that has a slight curve in one plane. This prismatic structure has overall dimensions on the order of tens of mm in length, tens of mm in width, and several mm in thickness, such that it may be disposed in a range of intervertebral spaces and provide a range of distraction, if so desired. Preferably, the prismatic structure defines one or more voids 18 in which a bone graft material or the like may selectively be disposed. These voids 18 may be internal to the prismatic structure, pass through the pair of opposed arcuate surfaces 12, pass through the pair of opposed frictional surfaces 14, and/or be in communication with one or more recesses 19 (FIG. 1) manufactured into the exterior of the pair of opposed arcuate surfaces 12 and/or the pair of opposed frictional surfaces 14. These voids 18 and/or recesses 19 help promote bony ingrowth that eventually fuses the intervertebral implant device 10 in the intervertebral space. One end of the intervertebral implant device 10 includes a rounded or partially-rounded end wall 20, that preferably has smoothed edges 21 to prevent it from catching on or damaging any anatomical structures during insertion. The other end of the intervertebral implant device 10 includes a recessed or fish-tailed end wall 22. The fish-tailed end wall 22 defines a hole and/or other retention structures 24 (FIG. 1) for selectively and pivotably receiving one or more surgical implantation devices. In this exemplary embodiment, the fish-tailed end wall 22 includes a pair of angularly disposed walls 23,25 joined by a central flat wall 27 (FIG. 1). The first of the pair of angularly disposed walls 23 protrudes from the prismatic structure to a greater degree than the second of the pair of angularly disposed walls 25, although other suitable configurations may be utilized. In this exemplary embodiment, the retention structures 24 for selectively and pivotably receiving one or more surgical implantation devices are coextensive with the one or more recesses 19 manufactured into the exterior of the pair of opposed arcuate surfaces 12 and/or the pair of opposed frictional surfaces 14. The intervertebral implant device 10 may be made of any suitable surgically-implantable material, such as a metallic material, a ceramic material, a polymeric material, or an allograft material, and may have any suitable dimensions such that it may be disposed within an intervertebral space of the spine of a patient while providing a desired degree of distraction.

Figure 3:
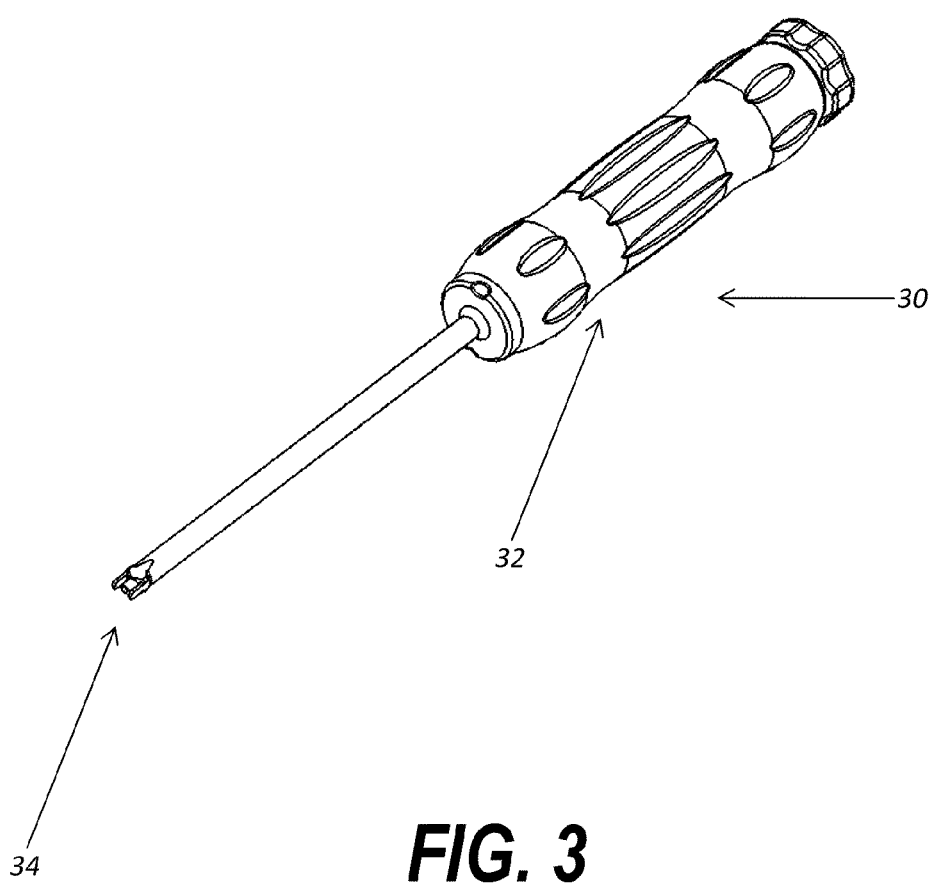
FIG. 3 is a perspective diagram illustrating one exemplary embodiment of a placement device for use with the intervertebral implant device of the present invention.

FIG. 3 is a perspective diagram illustrating one exemplary embodiment of a placement device 30 for use with the intervertebral implant device 10 (FIGS. 1 and 2) of the present invention. The placement device 30 includes a handle portion 32 and an engaging portion 34. Preferably, the engaging portion 34 includes a pillar and/or fin structures for selectively engaging the hole and/or other retention structures 24 (FIG. 1) of the intervertebral implant device 10, such that the intervertebral implant device 10 is selectively held by the placement device 30 while being inserted into the intervertebral space.

Figure 4:
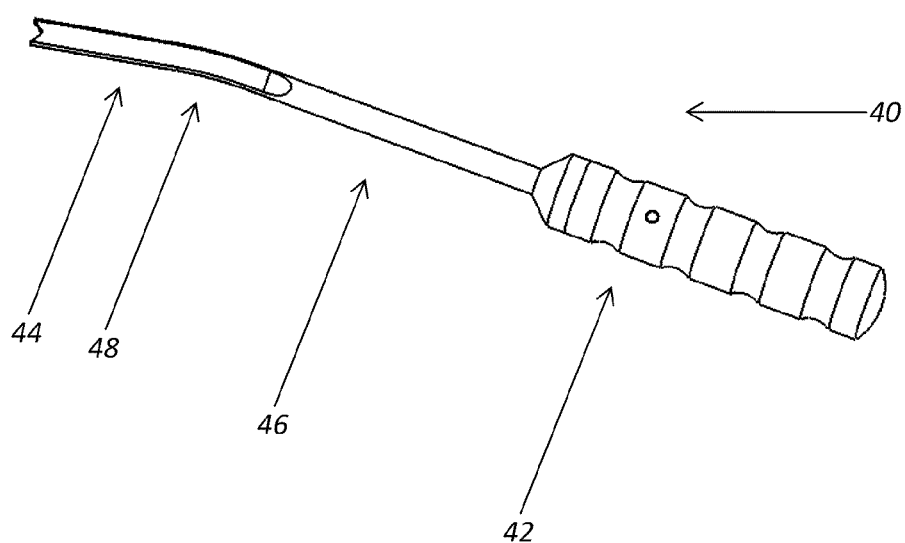
FIG. 4 is a perspective diagram illustrating one exemplary embodiment of a positioning device for use with the intervertebral implant device of the present invention.

FIG. 4 is a perspective diagram illustrating one exemplary embodiment of a positioning device 40 for use with the intervertebral implant device 10 (FIGS. 1 and 2) of the present invention. The positioning device 40 includes a handle portion 42 and an engaging portion 44. Preferably, the engaging portion 44 includes a fish-tailed feature for selectively engaging the fish-tailed end wall 22 (FIGS. 1 and 2) of the intervertebral implant device 10, such that the intervertebral implant device 10 is selectively guided by the positioning device 40 once inserted into the intervertebral space. Accordingly, the shaft 46 of the positioning device 40 includes a curved portion 48, allowing the positioning device 40 to be guided through a narrow transforaminal window (either left or right) and into the intervertebral space while in contact with the intervertebral implant device 10.

Figure 5:
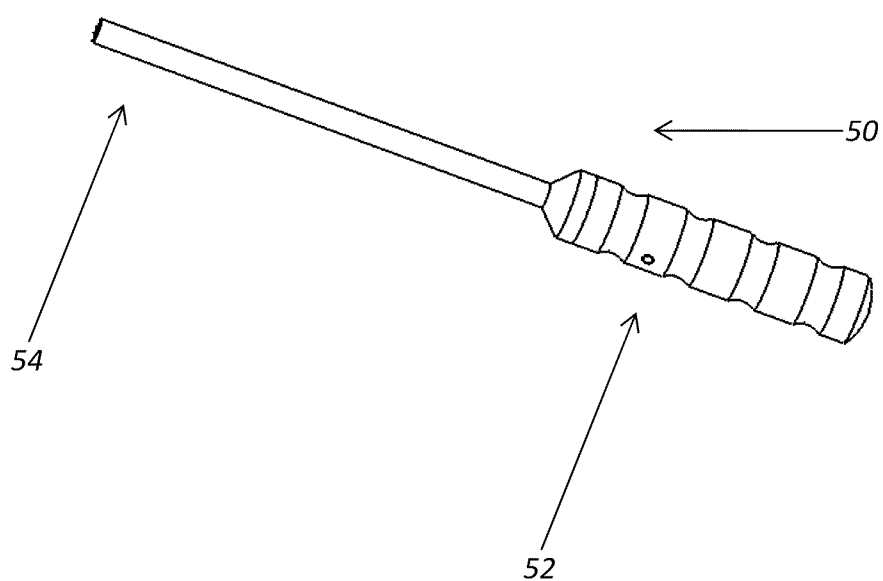
FIG. 5 is a perspective diagram illustrating one exemplary embodiment of a tamping device for use with the intervertebral implant device of the present invention.

FIG. 5 is a perspective diagram illustrating one exemplary embodiment of a tamping device 50 for use with the intervertebral implant device 10 (FIGS. 1 and 2) of the present invention. The tamping device 50 includes a handle portion 52 and an engaging portion 54. Preferably, the engaging portion 54 includes one or more friction structures for selectively engaging the fish-tailed end wall 22 (FIGS. 1 and 2) of the intervertebral implant device 10, such that the intervertebral implant device 10 is selectively driven by the tamping device 50 while being positioned and seated in the intervertebral space.

Figure 6:
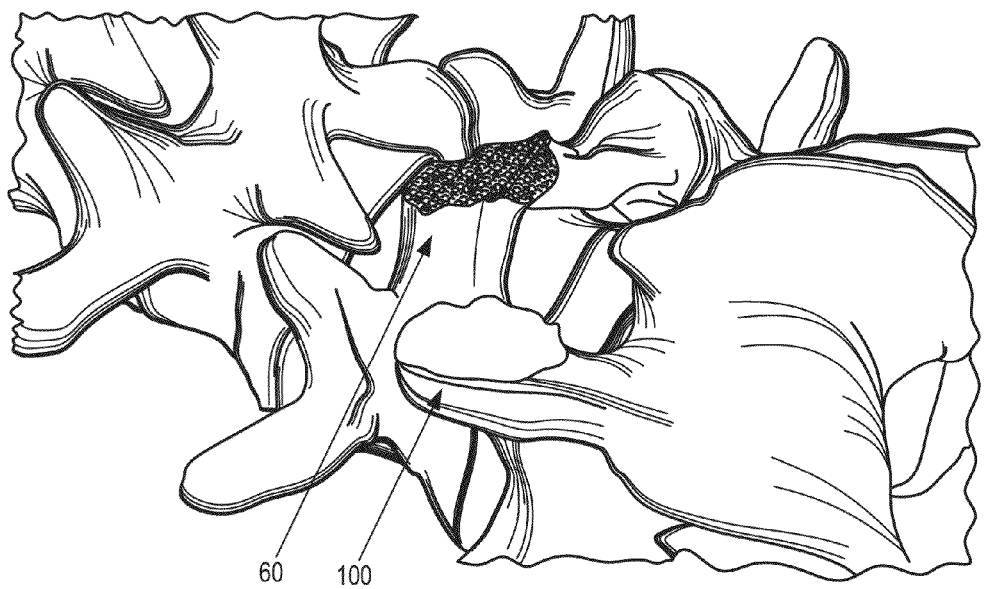
FIG. 6 is a series of perspective drawings illustrating successive steps in one exemplary embodiment of a method for surgically implanting the intervertebral implant device of the present invention—illustrating the removal of a small amount of bony material adjacent to a facet joint of the spine in order to form an access portal through which the intervertebral implant device of the present invention may be inserted into an intervertebral space.
Figure 6:
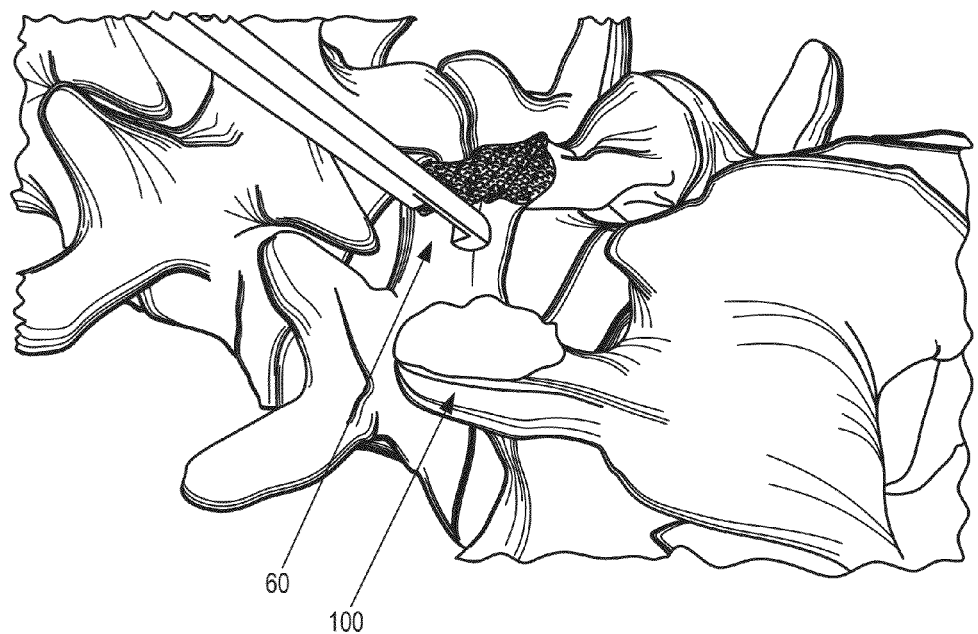

FIG. 6 is a series of perspective drawings illustrating successive steps in one exemplary embodiment of a method for surgically implanting the intervertebral implant device 10 (FIGS. 1 and 2) of the present invention—illustrating the removal of a small amount of bony material 60 adjacent to a facet joint 100 of the spine in order to form an access portal through which the intervertebral implant device 10 of the present invention may be inserted into an intervertebral space.

Figure 7:
FIG. 7 is a series of perspective drawings illustrating continuing successive steps in one exemplary embodiment of a method for surgically implanting the intervertebral implant device of the present invention—again illustrating the removal of a small amount of bony material adjacent to a facet joint of the spine in order to form an access portal through which the intervertebral implant device of the present invention may be inserted into an intervertebral space.

FIG. 7 is a series of perspective drawings illustrating continuing successive steps in one exemplary embodiment of a method for surgically implanting the intervertebral implant device 10 (FIGS. 1 and 2) of the present invention—again illustrating the removal of a small amount of bony material 70 adjacent to a facet joint 100 of the spine in order to form an access portal through which the intervertebral implant device 10 of the present invention may be inserted into an intervertebral space.

Figure 8:
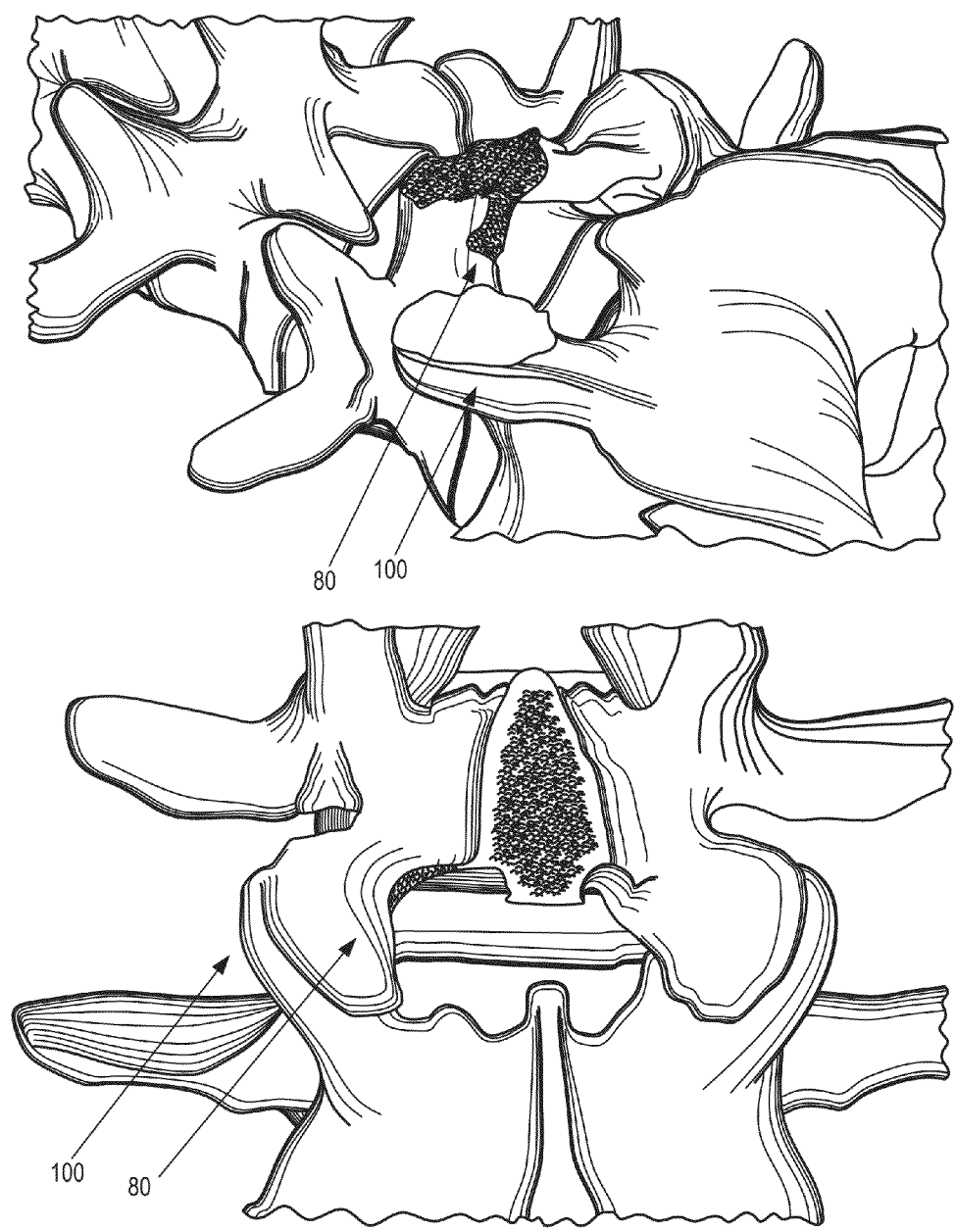
FIG. 8 is a series of perspective drawings illustrating continuing successive steps in one exemplary embodiment of a method for surgically implanting the intervertebral implant device of the present invention—again illustrating the removal of a small amount of bony material adjacent to a facet joint of the spine in order to form an access portal through which the intervertebral implant device of the present invention may be inserted into an intervertebral space.

FIG. 8 is a series of perspective drawings illustrating continuing successive steps in one exemplary embodiment of a method for surgically implanting the intervertebral implant device 10 (FIGS. 1 and 2) of the present invention—again illustrating the removal of a small amount of bony material 80 adjacent to a facet joint 100 of the spine in order to form an access portal through which the intervertebral implant device 10 of the present invention may be inserted into an intervertebral space.

Figure 9:
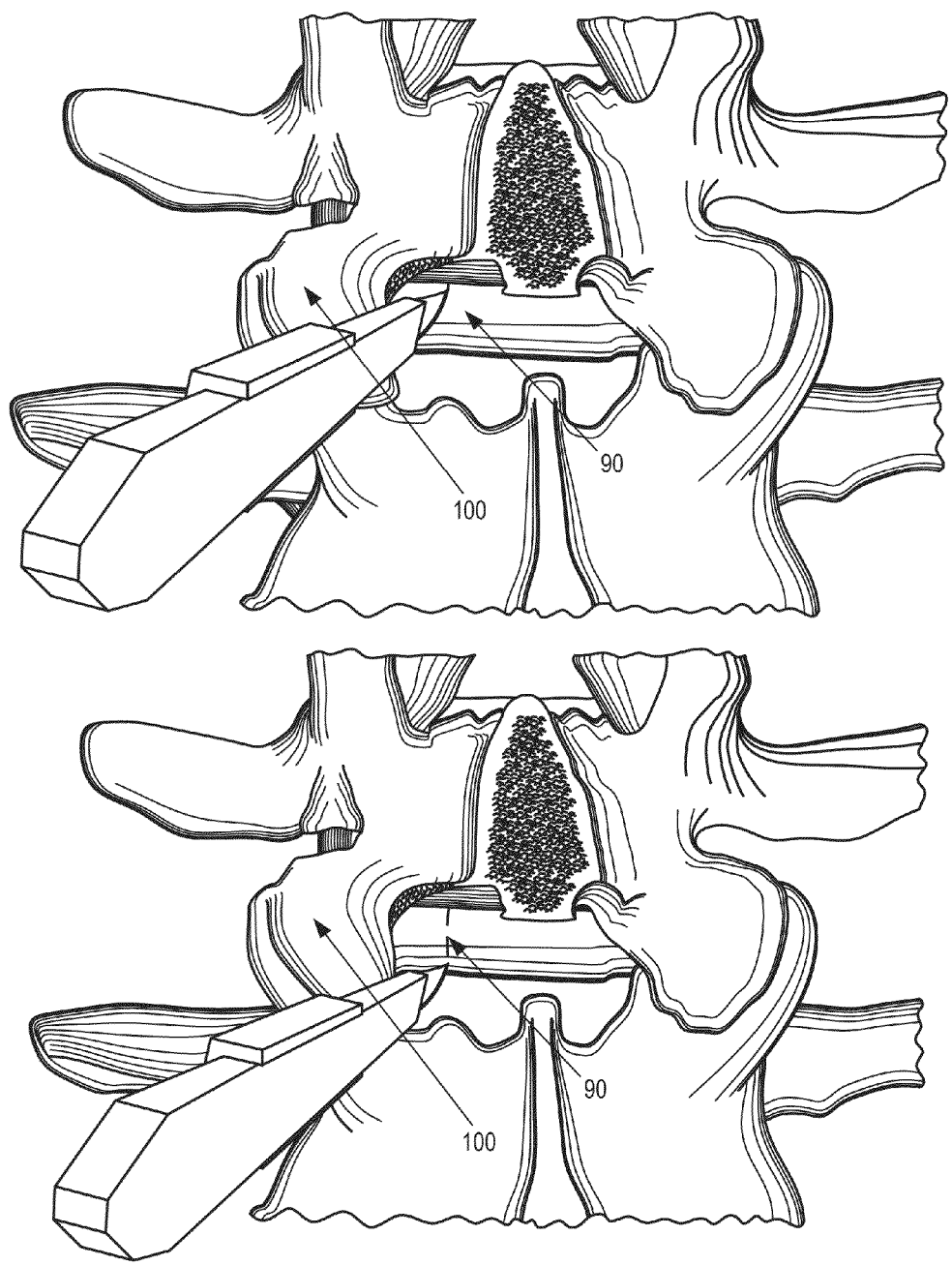
FIG. 9 is a series of perspective drawings illustrating continuing successive steps in one exemplary embodiment of a method for surgically implanting the intervertebral implant device of the present invention—illustrating the removal of a small amount of soft tissue material adjacent to a facet joint of the spine in order to form an access portal through which the intervertebral implant device of the present invention may be inserted into an intervertebral space.

FIG. 9 is a series of perspective drawings illustrating continuing successive steps in one exemplary embodiment of a method for surgically implanting the intervertebral implant device 10 (FIGS. 1 and 2) of the present invention—illustrating the removal of a small amount of soft tissue material 90 adjacent to a facet joint 100 of the spine in order to form an access portal through which the intervertebral implant device 10 of the present invention may be inserted into an intervertebral space.

Figure 10:
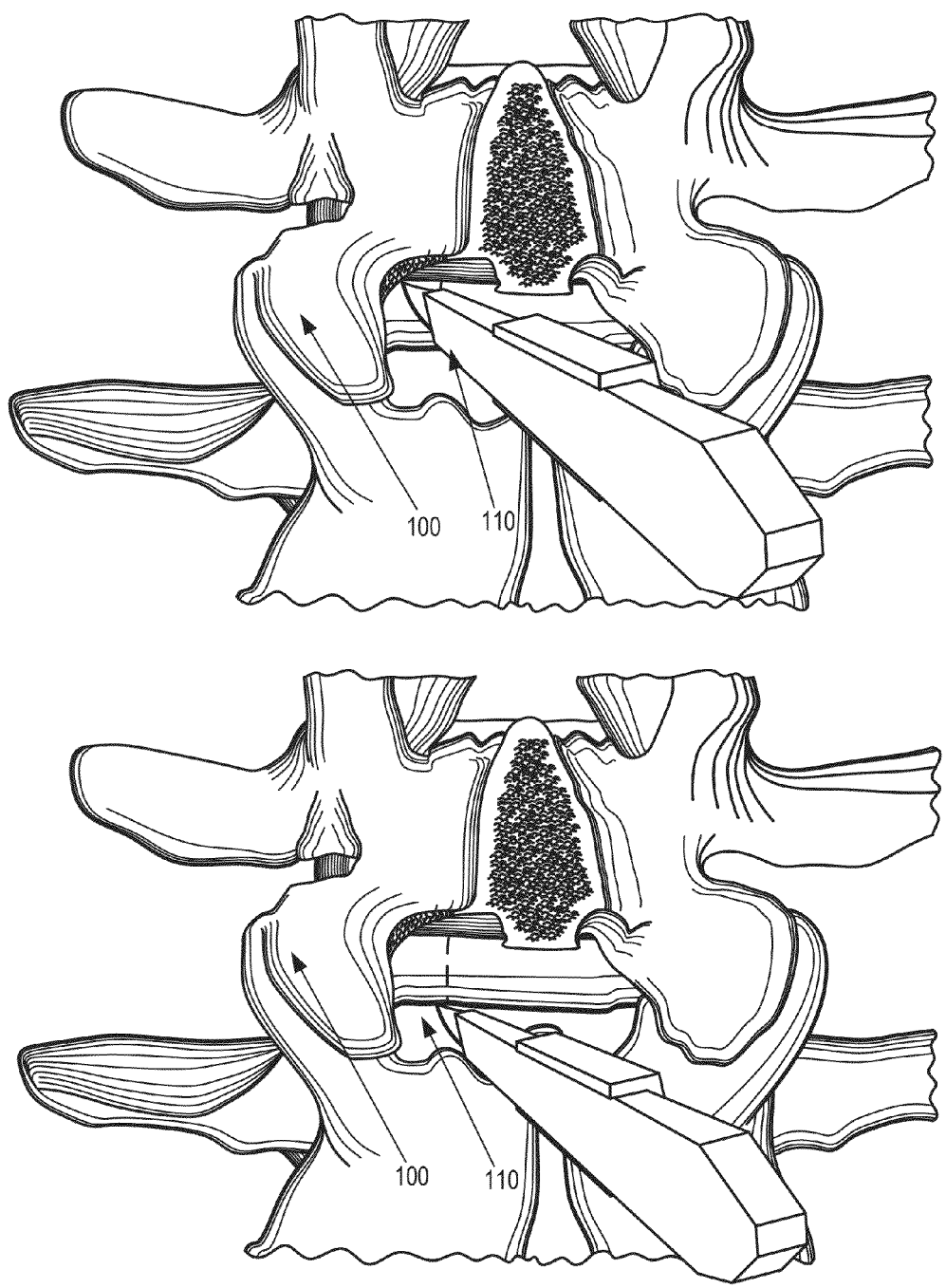
FIG. 10 is a series of perspective drawings illustrating continuing successive steps in one exemplary embodiment of a method for surgically implanting the intervertebral implant device of the present invention—again illustrating the removal of a small amount of soft tissue material adjacent to a facet joint of the spine in order to form an access portal through which the intervertebral implant device of the present invention may be inserted into an intervertebral space.

FIG. 10 is a series of perspective drawings illustrating continuing successive steps in one exemplary embodiment of a method for surgically implanting the intervertebral implant device 10 (FIGS. 1 and 2) of the present invention—again illustrating the removal of a small amount of soft tissue material 110 adjacent to a facet joint 100 of the spine in order to form an access portal through which the intervertebral implant device 10 of the present invention may be inserted into an intervertebral space.

Figure 11:
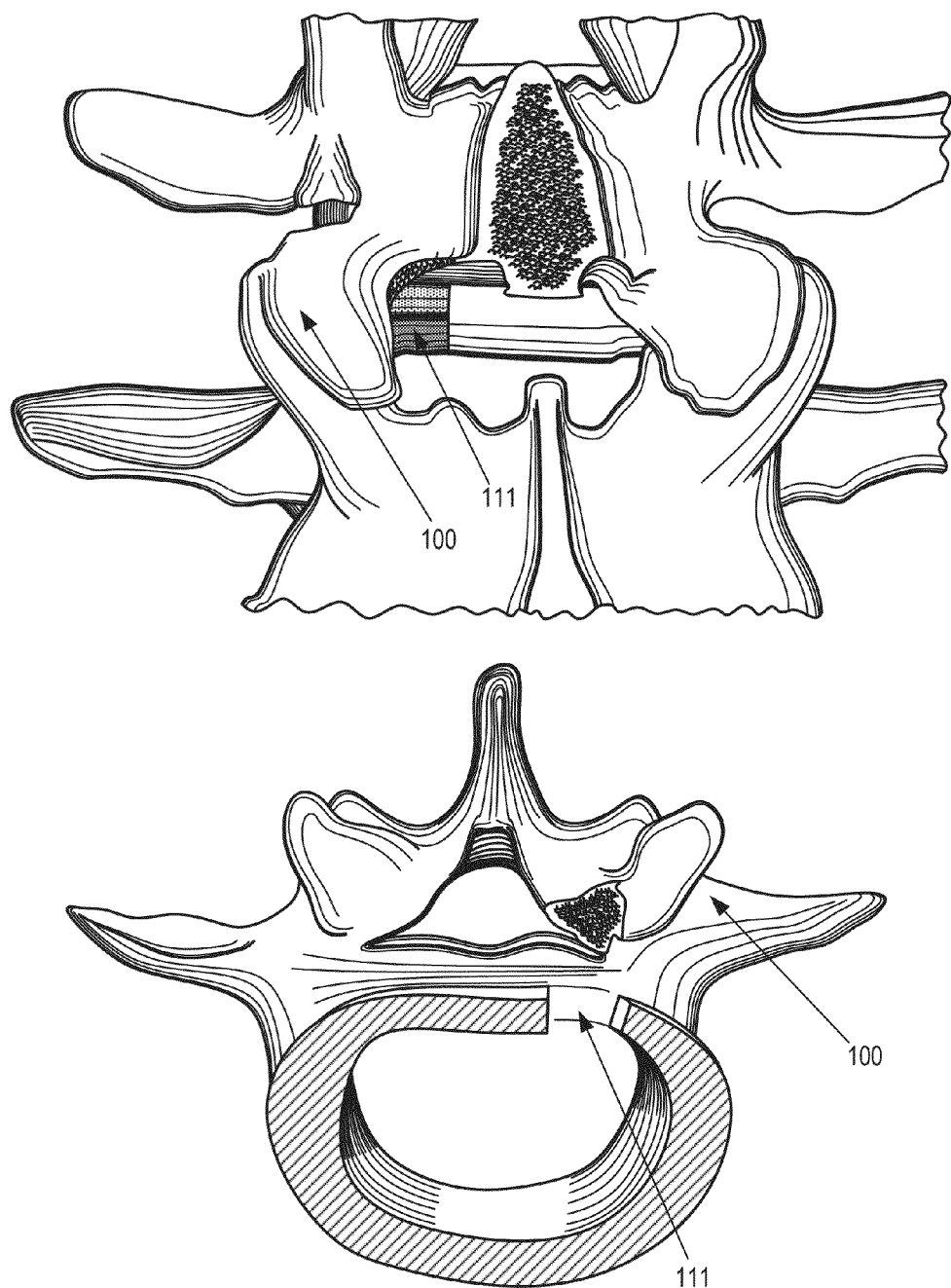
FIG. 11 is a series of perspective drawings illustrating continuing successive steps in one exemplary embodiment of a method for surgically implanting the intervertebral implant device of the present invention—again illustrating the removal of a small amount of soft tissue material adjacent to a facet joint of the spine in order to form an access portal through which the intervertebral implant device of the present invention may be inserted into an intervertebral space.

FIG. 11 is a series of perspective drawings illustrating continuing successive steps in one exemplary embodiment of a method for surgically implanting the intervertebral implant device 10 (FIGS. 1 and 2) of the present invention—again illustrating the removal of a small amount of soft tissue material 111 adjacent to a facet joint 100 of the spine in order to form an access portal through which the intervertebral implant device 10 of the present invention may be inserted into an intervertebral space.

Figure 12:
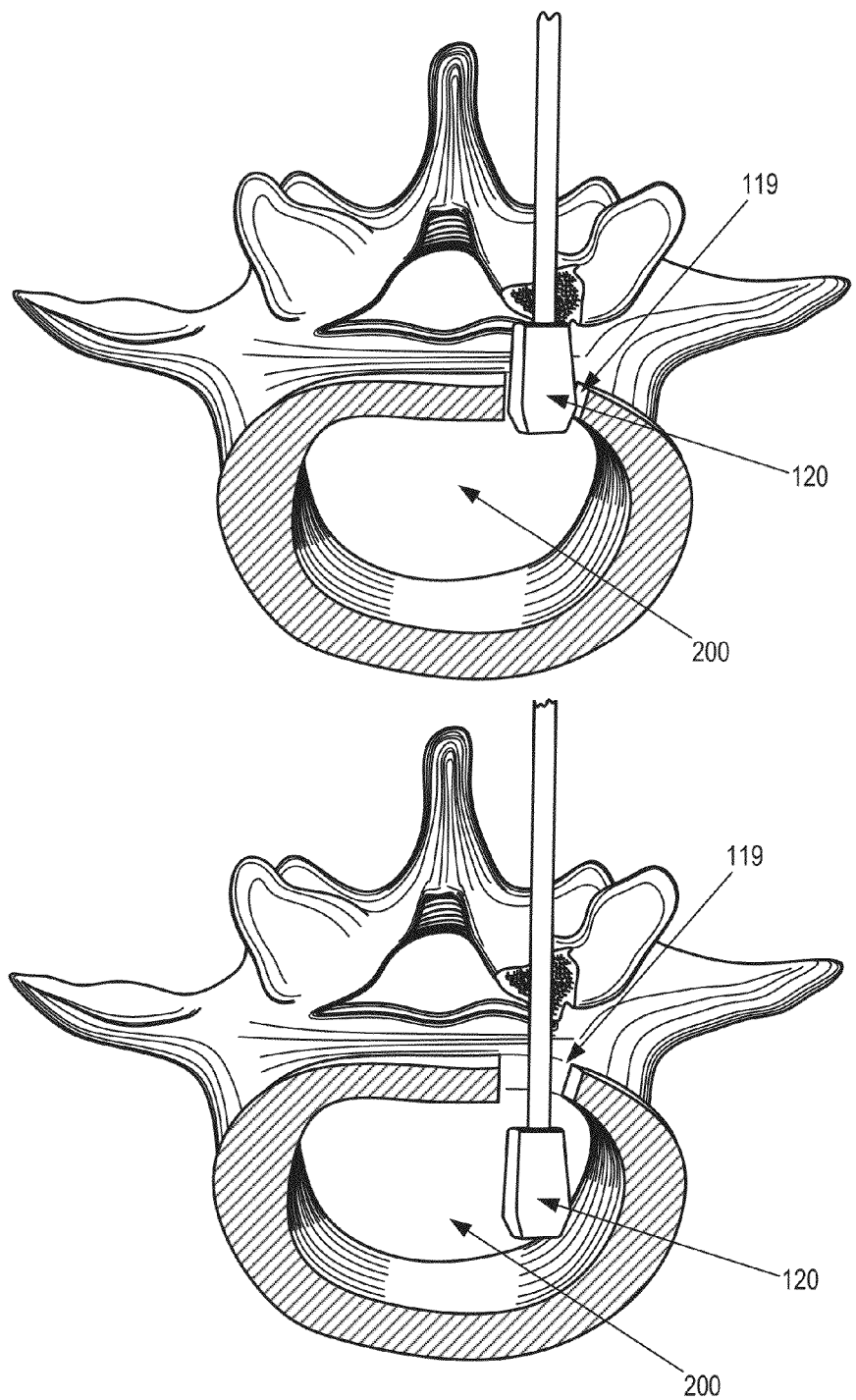
FIG. 12 is a series of perspective drawings illustrating continuing successive steps in one exemplary embodiment of a method for surgically implanting the intervertebral implant device of the present invention—illustrating the sizing of the intervertebral space prior to the insertion of the intervertebral implant device of the present invention.

FIG. 12 is a series of perspective drawings illustrating continuing successive steps in one exemplary embodiment of a method for surgically implanting the intervertebral implant device 10 (FIGS. 1 and 2) of the present invention—illustrating the sizing of the narrow transforaminal window 119 and intervertebral space 200 using a sizing device 120 prior to the insertion of the intervertebral implant device 10 of the present invention.

Figure 13:
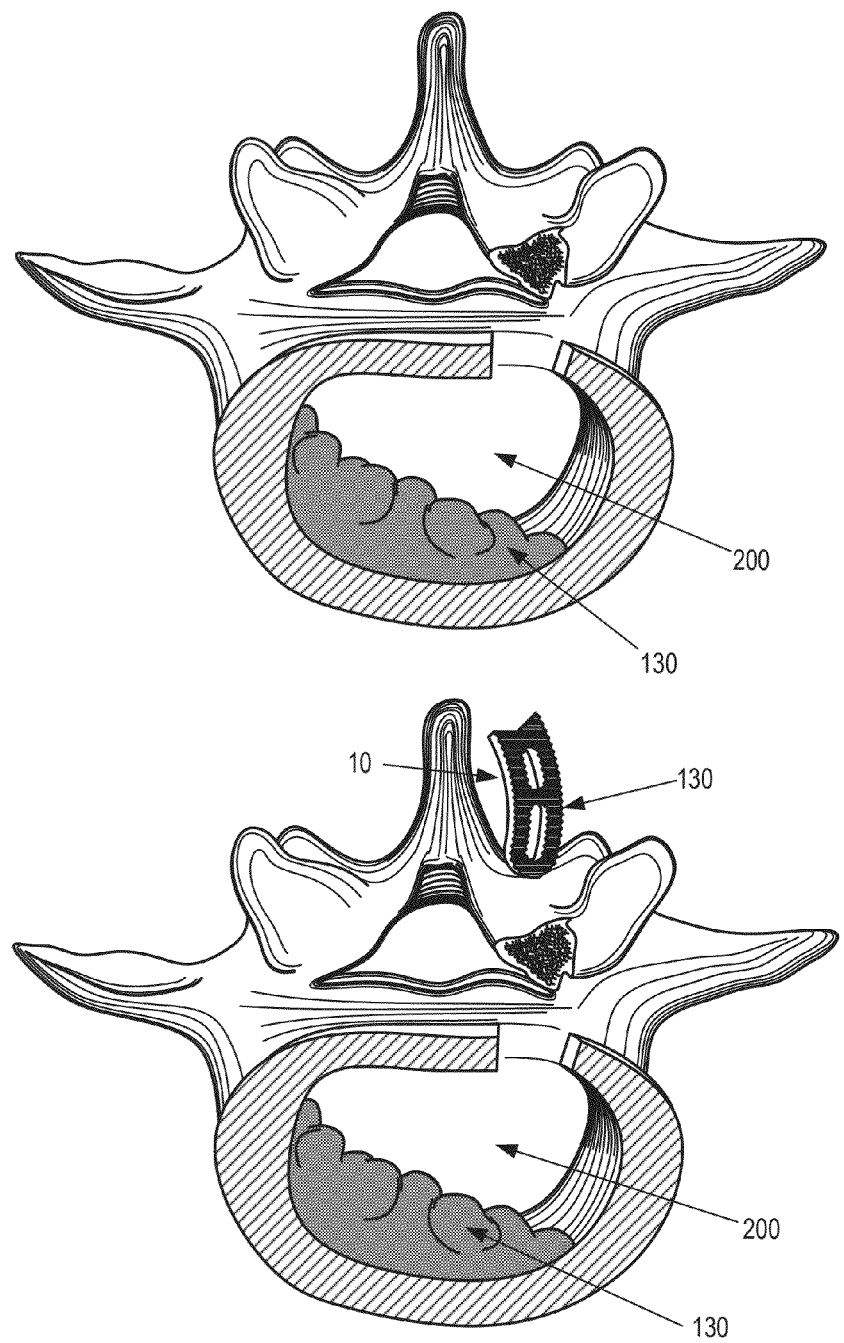
FIG. 13 is a series of perspective drawings illustrating continuing successive steps in one exemplary embodiment of a method for surgically implanting the intervertebral implant device of the present invention—illustrating the insertion of bone graft material into the intervertebral space prior to the insertion of the intervertebral implant device of the present invention.

FIG. 13 is a series of perspective drawings illustrating continuing successive steps in one exemplary embodiment of a method for surgically implanting the intervertebral implant device 10 of the present invention—illustrating the insertion of bone graft material 130 into the intervertebral space 200 prior to the insertion of the intervertebral implant device 10 of the present invention. In this exemplary embodiment, the intervertebral implant device is also packed with bone graft material 130.

Figure 14:
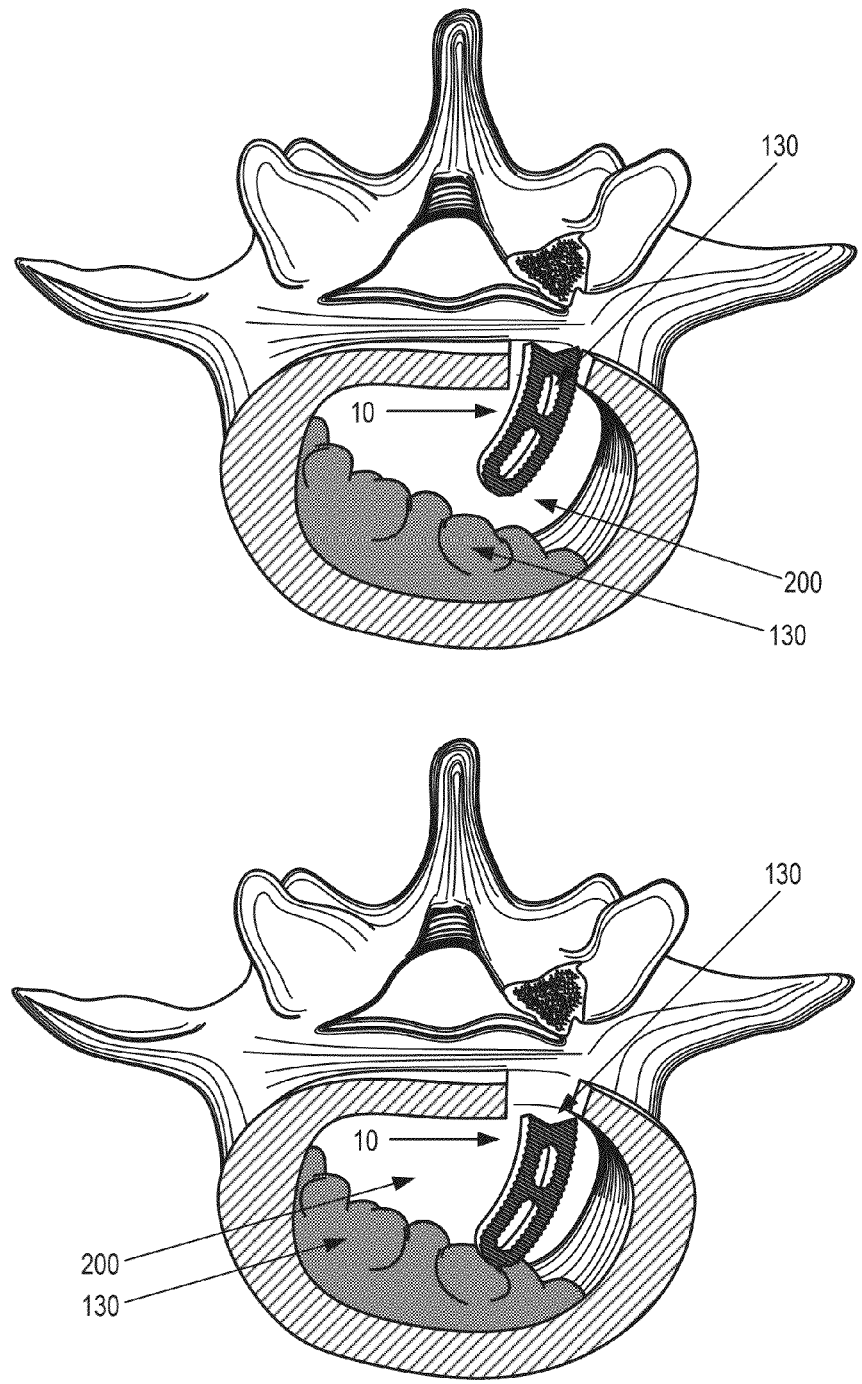
FIG. 14 is a series of perspective drawings illustrating continuing successive steps in one exemplary embodiment of a method for surgically implanting the intervertebral implant device of the present invention—illustrating the insertion of the intervertebral implant device of the present invention into the intervertebral space using the placement device of the present invention.

FIG. 14 is a series of perspective drawings illustrating continuing successive steps in one exemplary embodiment of a method for surgically implanting the intervertebral implant device 10 of the present invention—illustrating the insertion of the intervertebral implant device 10 of the present invention into the intervertebral space 200 using the placement device 30 (FIG. 3) of the present invention, for example.

Figure 15:
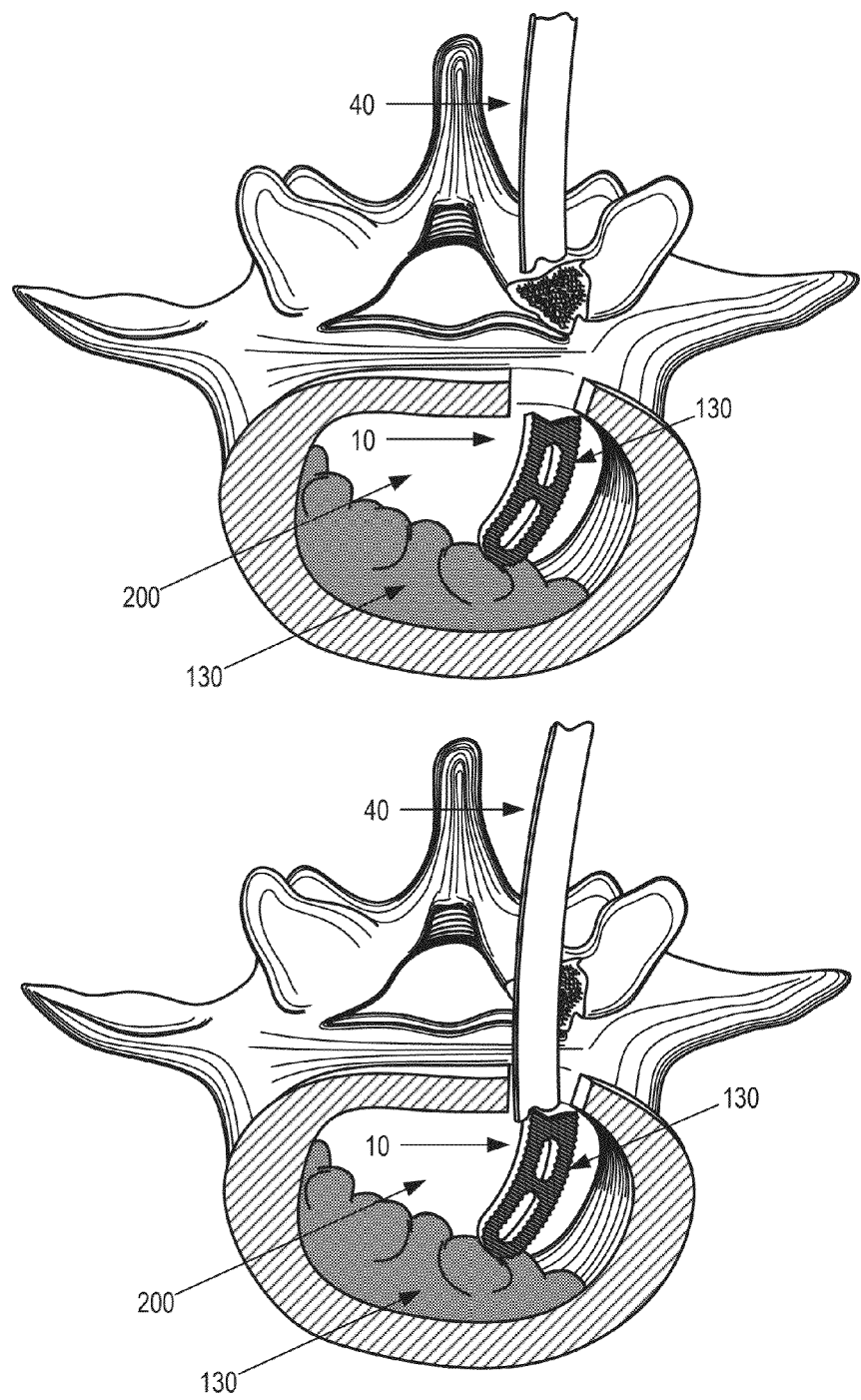
FIG. 15 is a series of perspective drawings illustrating continuing successive steps in one exemplary embodiment of a method for surgically implanting the intervertebral implant device of the present invention—illustrating the insertion and positioning of the intervertebral implant device of the present invention into and within the intervertebral space using the positioning device of the present invention.

FIG. 15 is a series of perspective drawings illustrating continuing successive steps in one exemplary embodiment of a method for surgically implanting the intervertebral implant device 10 of the present invention—illustrating the insertion and positioning of the intervertebral implant device 10 of the present invention into and within the intervertebral space 200 using the positioning device 40 of the present invention.

Figure 16:
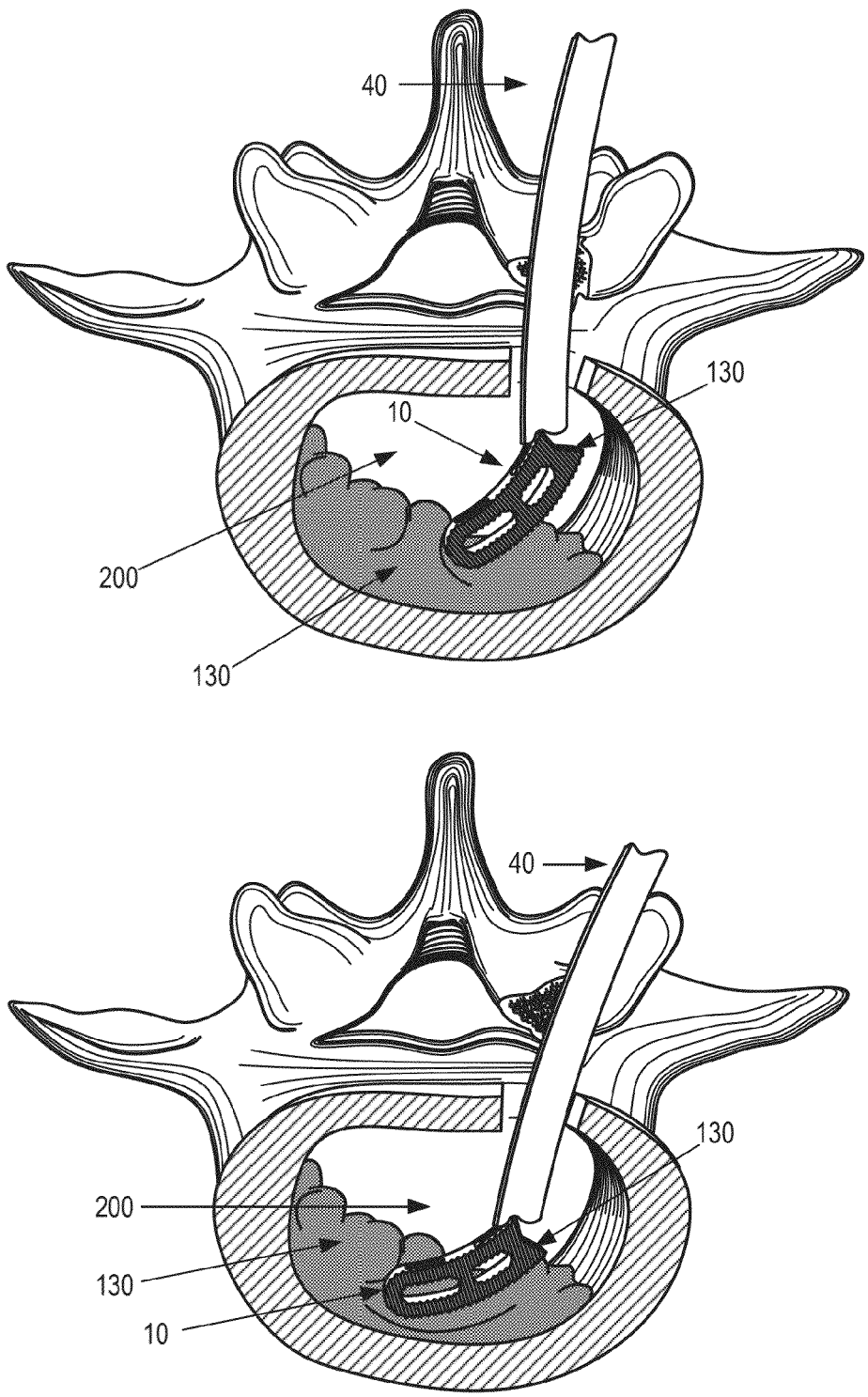
FIG. 16 is a series of perspective drawings illustrating continuing successive steps in one exemplary embodiment of a method for surgically implanting the intervertebral implant device of the present invention—again illustrating the insertion and positioning of the intervertebral implant device of the present invention into and within the intervertebral space using the positioning device of the present invention.

FIG. 16 is a series of perspective drawings illustrating continuing successive steps in one exemplary embodiment of a method for surgically implanting the intervertebral implant device 10 of the present invention—again illustrating the insertion and positioning of the intervertebral implant device 10 of the present invention into and within the intervertebral space 200 using the positioning device 40 of the present invention.

Figure 17:
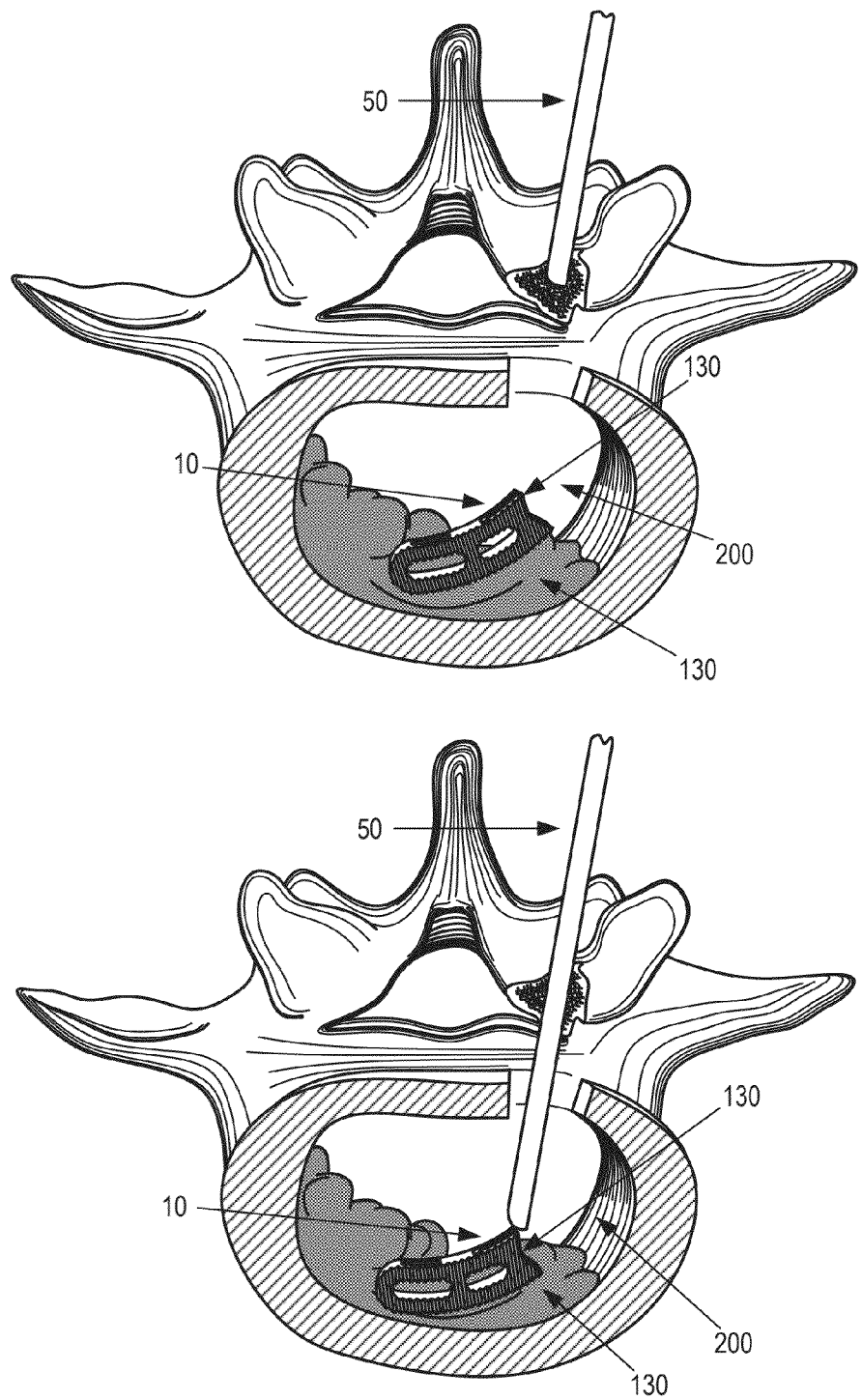
FIG. 17 is a series of perspective drawings illustrating continuing successive steps in one exemplary embodiment of a method for surgically implanting the intervertebral implant device of the present invention—illustrating the insertion and positioning of the intervertebral implant device of the present invention into and within the intervertebral space using the tamping device of the present invention.

FIG. 17 is a series of perspective drawings illustrating continuing successive steps in one exemplary embodiment of a method for surgically implanting the intervertebral implant device 10 of the present invention—illustrating the insertion and positioning of the intervertebral implant device 10 of the present invention into and within the intervertebral space 200 using the tamping device 50 of the present invention.

Figure 18:
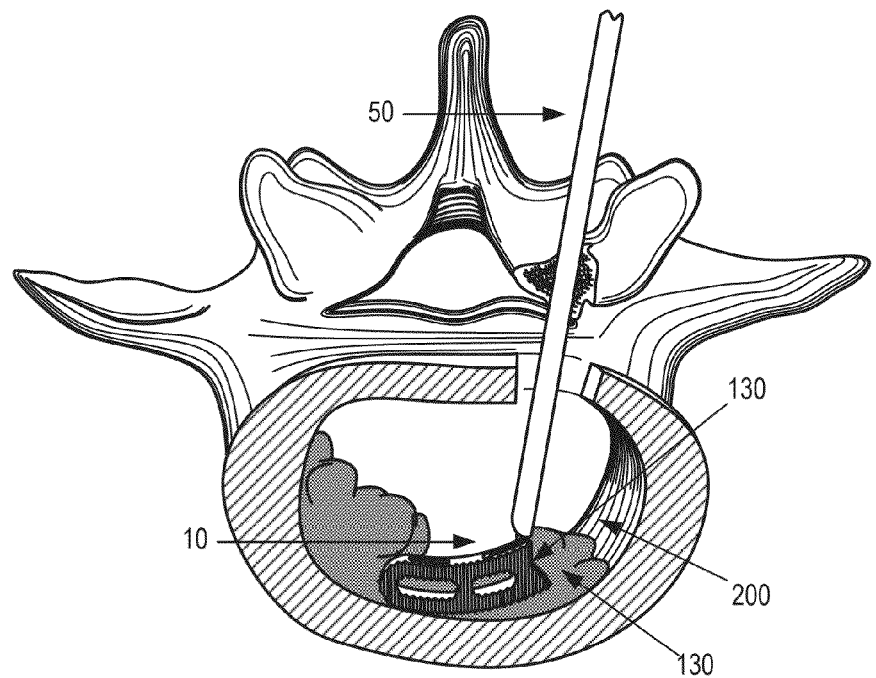
FIG. 18 is a series of perspective drawings illustrating continuing successive steps in one exemplary embodiment of a method for surgically implanting the intervertebral implant device of the present invention—again illustrating the insertion and positioning of the intervertebral implant device of the present invention into and within the intervertebral space again using the tamping device of the present invention.
Figure 18:
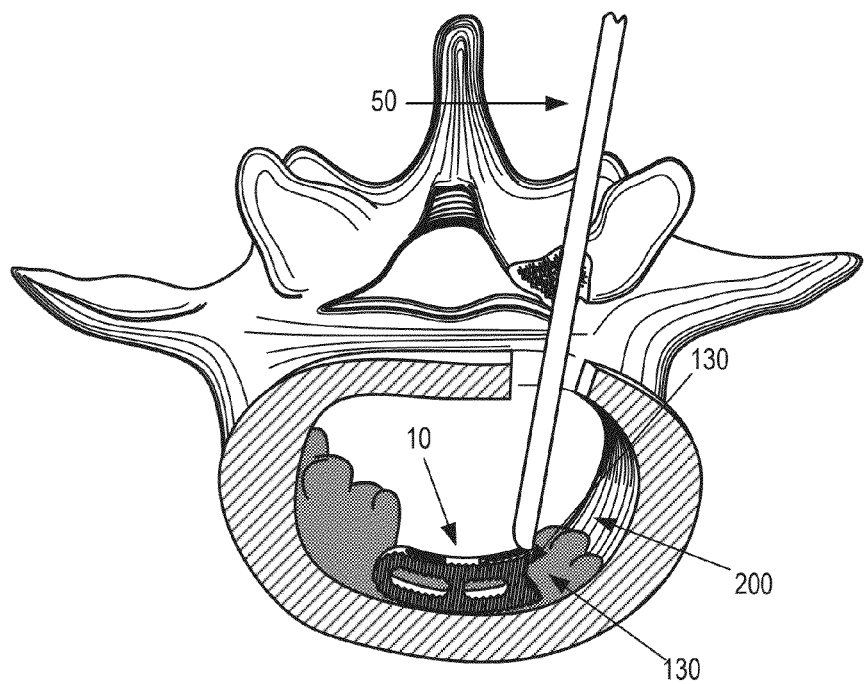

FIG. 18 is a series of perspective drawings illustrating continuing successive steps in one exemplary embodiment of a method for surgically implanting the intervertebral implant device 10 of the present invention—again illustrating the insertion and positioning of the intervertebral implant device 10 of the present invention into and within the intervertebral space 200 again using the tamping device 50 of the present invention.

Figure 19:
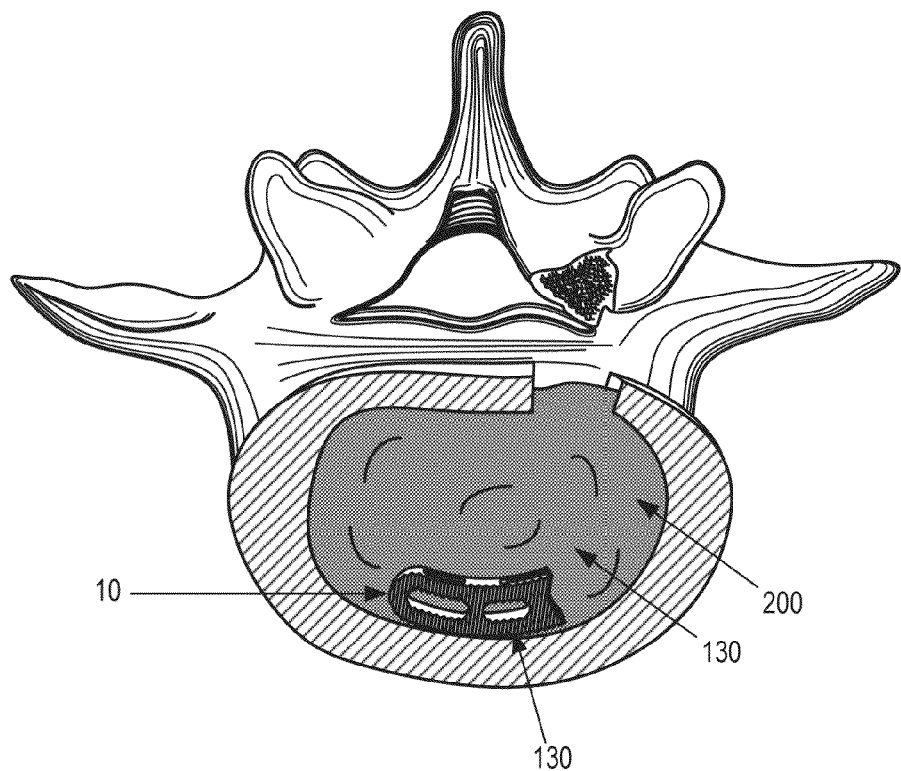
FIG. 19 is a final perspective drawing illustrating a continuing successive step in one exemplary embodiment of a method for surgically implanting the intervertebral implant device of the present invention—illustrating the final placement of the intervertebral implant device in the intervertebral space, along with the associated bone graft material.

FIG. 19 is a final perspective drawing illustrating a continuing successive step in one exemplary embodiment of a method for surgically implanting the intervertebral implant device 10 of the present invention—illustrating the final placement of the intervertebral implant device 10 in the intervertebral space 200, along with the associated bone graft material 130.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims. In this respect, this specification is intended to be exemplary and non-limiting to the greatest extent possible.

What is claimed is:

1. An intervertebral implant device, comprising:
a pair of opposed arcuate surfaces;
a pair of opposed frictional surfaces each comprising a plurality of raised structures;
a first end wall joining the pair of opposed arcuate surfaces; and
a second end wall recessed at least in part and joining the pair of opposed arcuate surfaces, the second end wall comprising a first wall portion and a second wall portion arranged at an angle to one another and collectively forming a fish-tailed structure when viewed from one of the opposed frictional surfaces, wherein the fish-tailed structure is formed so as to extend at least substantially uninterrupted between the opposed arcuate surfaces;
wherein the intervertebral implant device defines one or more voids configured to selectively receive a bone graft material.

2. The intervertebral implant device of claim 1, wherein the second end wall is configured to selectively and pivotably receive one or more surgical implantation devices.

3. The intervertebral implant device of claim 1, wherein the first-end wall comprises one or more smoothed edges.

4. The intervertebral implant device of claim 1, wherein the second at least partially recessed end wall comprises one or more of a hole and a recess configured to selectively receive a surgical tool.

5. The intervertebral implant device of claim 1, wherein the one or more voids defined by the intervertebral implant device pass through one or more of the pair of opposed arcuate surfaces and the pair of opposed frictional surfaces.

6. The intervertebral implant device of claim 1, wherein the intervertebral implant device is configured to be selectively disposed in an intervertebral space through an access window formed through bony and soft tissue structures to either the left or right of a centerline of a spine.

7. The intervertebral implant device of claim 1, wherein the first end wall is curved at least in part.

8. The intervertebral implant device of claim 1, wherein the second end wall further comprises a third wall portion positioned in between and joining the first and second wall portions.

9. The intervertebral implant device of claim 8, wherein the third wall portion is at least substantially flat.

10. The intervertebral implant device of claim 1, wherein the first wall portion protrudes from the intervertebral implant device to a greater degree than the second wall portion.

11. The intervertebral implant device of claim 10, wherein the second end wall further comprises a third wall portion positioned in between and joining the first and second wall portions.

12. The intervertebral implant device of claim 11, wherein the first wall portion extends from the third wall portion a greater distance than a distance with which the second wall portion extends.

13. The intervertebral implant device of claim 1, wherein the first wall portion directly connects with the second wall portion.

14. The intervertebral implant device of claim 1, wherein the fish-tailed structure is formed so as to extend at least substantially uninterrupted between the opposed frictional surfaces.

15. An intervertebral implant device, comprising:
a pair of opposed arcuate surfaces;
a pair of opposed frictional surfaces each comprising a plurality of raised structures;
a first end wall joining the pair of opposed arcuate surfaces; and
a second end wall recessed at least in part and joining the pair of opposed arcuate surfaces, the second end wall comprising a first wall portion and a second wall portion arranged at an angle to one another and collectively forming a fish-tailed structure, wherein the fish-tailed structure is formed so as to extend at least substantially uninterrupted along at least one dimension of the second end wall;
wherein the first wall portion extends between the opposed frictional surfaces from an upper frictional surface to a lower frictional surface, and wherein the second wall portion extends between the opposed frictional surfaces from the upper frictional surface to the lower frictional surface.

16. The intervertebral implant device of claim 15, further comprising at least one void configured to receive a bone graft material.

17. The intervertebral implant device of claim 15, wherein the first end wall is curved at least in part.

18. The intervertebral implant device of claim 15, wherein the fish-tailed structure is formed so as to extend at least substantially uninterrupted between the opposed arcuate surfaces.

19. An intervertebral implant device, comprising:
a first sidewall;
a second sidewall opposite from the first sidewall;
a pair of opposed frictional surfaces each comprising a plurality of raised structures;
a first end wall joining the pair of opposed sidewall surfaces; and a second end wall recessed at least in part and joining the first sidewall and the second sidewall, the second end wall comprising a first wall portion and a second wall portion arranged at an angle to one another and collectively forming a fish-tailed structure, wherein the fish-tailed structure is formed so as to extend at least substantially uninterrupted between the first sidewall and the second sidewall, and wherein the fish-tailed structure is formed so as to extend at least substantially uninterrupted between the opposed frictional surfaces;

wherein the first wall portion extends from and joins with the first sidewall, and wherein the second wall portion extends from and joins with the second sidewall so as to form the fish-tailed structure.

20. The intervertebral implant device of claim 19, wherein the first sidewall is arcuate.

21. The intervertebral implant device of claim 20, wherein the second sidewall is arcuate.

22. The intervertebral implant device of claim 19, wherein the first sidewall is at least substantially parallel to the second sidewall.

23. The intervertebral implant device of claim 22, wherein the first sidewall is parallel to the second sidewall along the entire lengths of the first and second sidewalls.

24. The intervertebral implant device of claim 19, wherein the intervertebral implant device comprises a ceramic material.

* * * * *